United States Patent
Keselowsky et al.

(10) Patent No.: US 9,012,202 B2
(45) Date of Patent: *Apr. 21, 2015

(54) CELL-BASED ARRAYS, METHODS OF MAKING, AND METHODS OF USING

(75) Inventors: Benjamin George Keselowsky, Gainesville, FL (US); Abhinav Prakash Acharya, Gainesville, FL (US); Emina Huang, Gainesville, FL (US); Edward William Scott, Gainesville, FL (US); Matthew Carstens, Gainesville, FL (US)

(73) Assignee: University of Florida Research Foundation, Inc.

( * ) Notice: Subject to any disclaimer, the term of this patent is extended or adjusted under 35 U.S.C. 154(b) by 226 days.

This patent is subject to a terminal disclaimer.

(21) Appl. No.: 13/373,051

(22) Filed: Nov. 2, 2011

(65) Prior Publication Data
US 2012/0108468 A1 May 3, 2012

Related U.S. Application Data

(60) Provisional application No. 61/409,223, filed on Nov. 2, 2010.

(51) Int. Cl.
| C12M 1/00 | (2006.01) |
| C12M 1/34 | (2006.01) |
| C12Q 1/00 | (2006.01) |
| G01N 33/53 | (2006.01) |
| C40B 30/06 | (2006.01) |
| C40B 40/10 | (2006.01) |
| G01N 33/543 | (2006.01) |

(52) U.S. Cl.
CPC .................. *G01N 33/54366* (2013.01)

(58) Field of Classification Search
USPC ............ 435/4, 6.1, 7.1, 283.1, 287.2; 506/10, 506/18
See application file for complete search history.

(56) References Cited

U.S. PATENT DOCUMENTS

| 6,406,745 | B1 * | 6/2002 | Talton ........................... 427/213 |
| 2003/0032203 | A1 * | 2/2003 | Sabatini et al. ............... 436/518 |
| 2006/0251701 | A1 * | 11/2006 | Lynn et al. .................... 424/426 |
| 2009/0258057 | A1 * | 10/2009 | Swiston et al. ............... 424/444 |

FOREIGN PATENT DOCUMENTS

WO    WO2008/086228    * 7/2008

OTHER PUBLICATIONS

Acharya et al 2008, Adhesive substrate-modulation of adaptive immune responses, 2008, Biomaterials, 29, 4736-4750.*
Acharya et al 2009, A high-throughput microparticle microarray platform for dendritic cell-targeting vaccines, 2009, Biomaterials, 30, 4168-4177.*

(Continued)

*Primary Examiner* — Narayan Bhat
(74) *Attorney, Agent, or Firm* — Thomas Horstemeyer, LLP

(57) ABSTRACT

Embodiments of the present disclosure provide for arrays, systems, and methods for the analyzing cells, methods of making arrays, and the like.

17 Claims, 15 Drawing Sheets a-a plane

(56) References Cited

OTHER PUBLICATIONS

Kristensen et al, Photoelectron Spectroscopy Studies of the Functionalization of a Silicon Surface with a Phosphorylcholine-Terminated Polymer Grafted onto (3-Aminopropyl)trimethoxysilane, 2006, Langmuir, 22, 9651-9657.*

Olenych et al, Fibronectin and Cell Attachment to Cell and Protein Resistant Polyelectrolyte Surfaces, 2005, Biomacromolecules, 6, 3252-3258.*

Carot et al, Structure of Mixed Carboxylic Acid Terminated Self-Assembled Monolayers: Experimental and Theoretical Investigation, 2007, J. Phys. Chem. C, 111, 4294-4304.*

Rammelt et al, Coating of titanium implants with collagen, RGD peptide and chondroitin sulfate, 2006, Biomaterials, 27, 5561-5571.*

Dekeyser et al, A rough morphology of the adsorbed fibronectin layer favors adhesion of neuronal cells, 2007, Journal of Biomedical Materials Research Part A, pp. 116-128.*

* cited by examiner

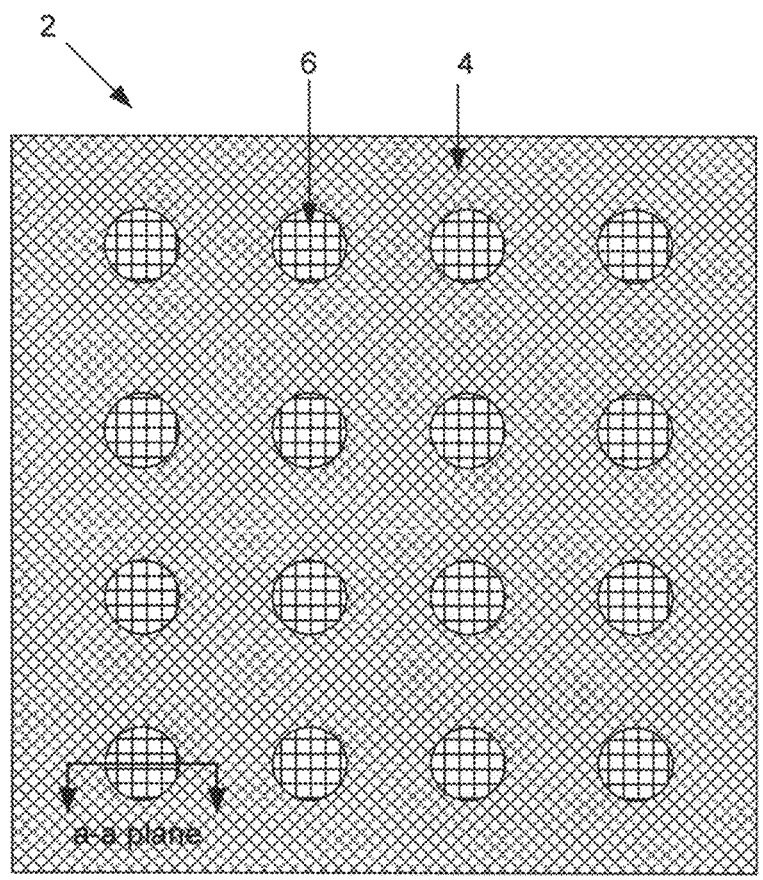
FIG. 1.1
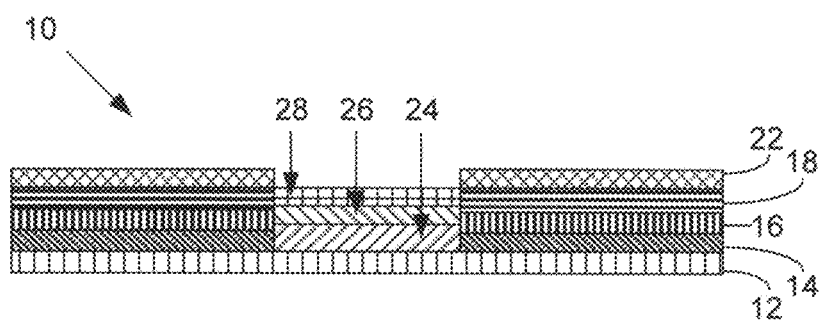
FIG. 1.2
a-a plane

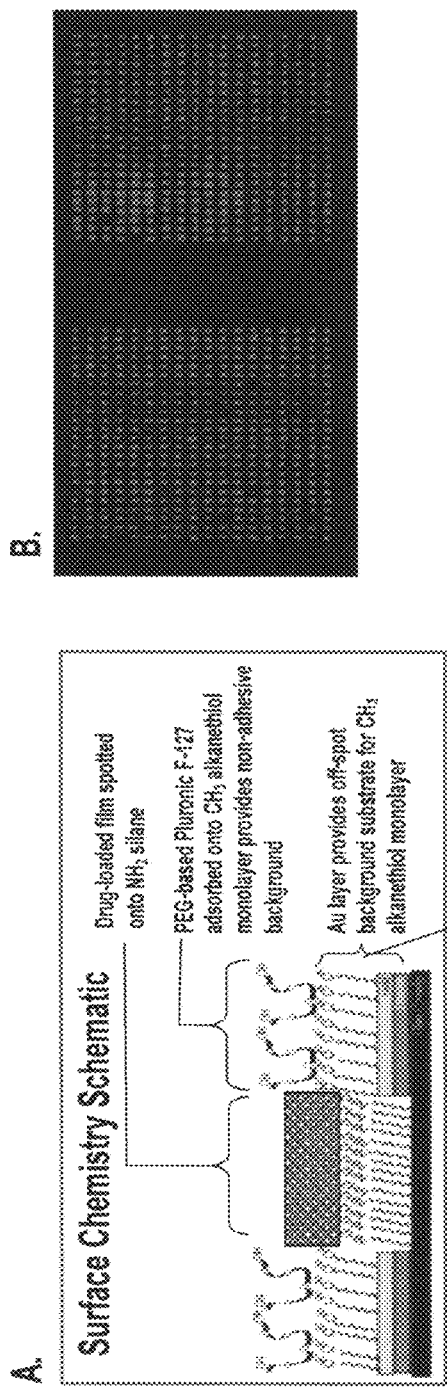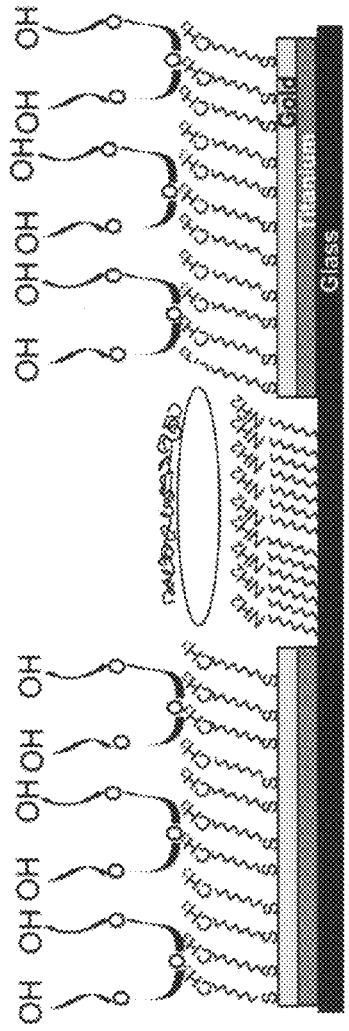
FIG. 1.3
Array Fabrication Schematic. A. Surface chemistry schematic is shown of a single arrayed spot. B. Representative microarray illustrating more than 1,000 spots arrayed onto a standard glass slide.

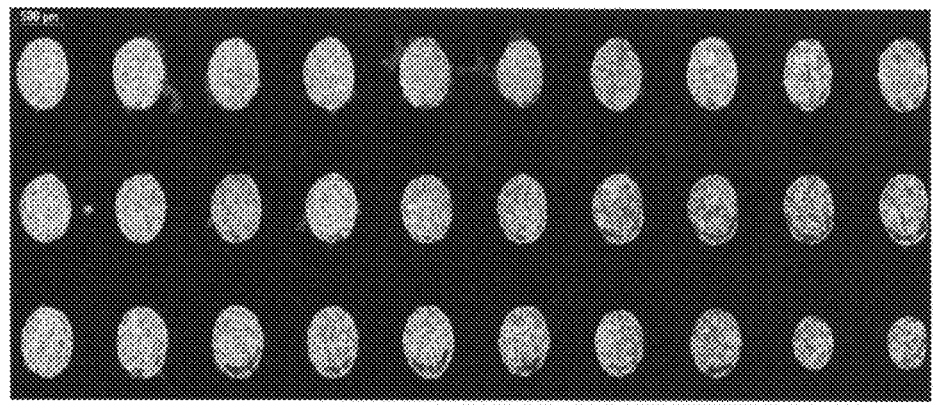
FIG. 2.1
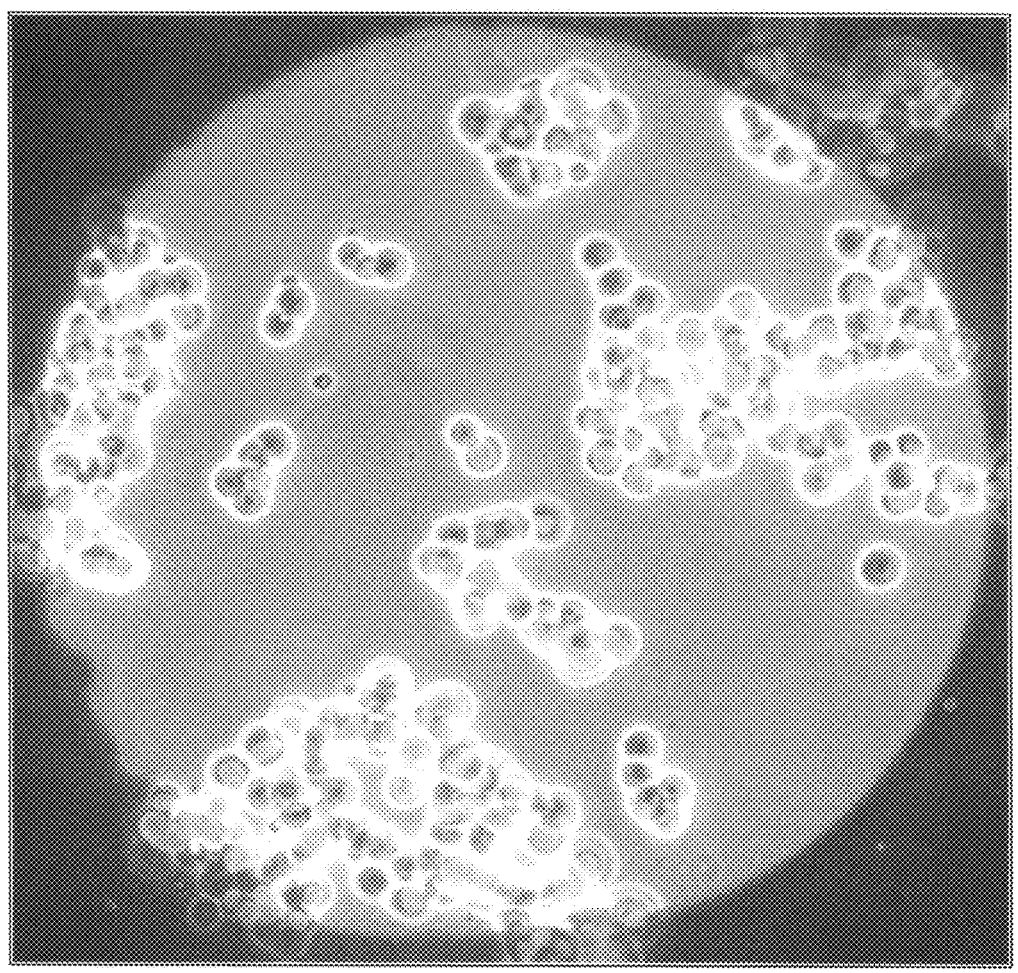
FIG. 2.2A

FIG. 2.2B

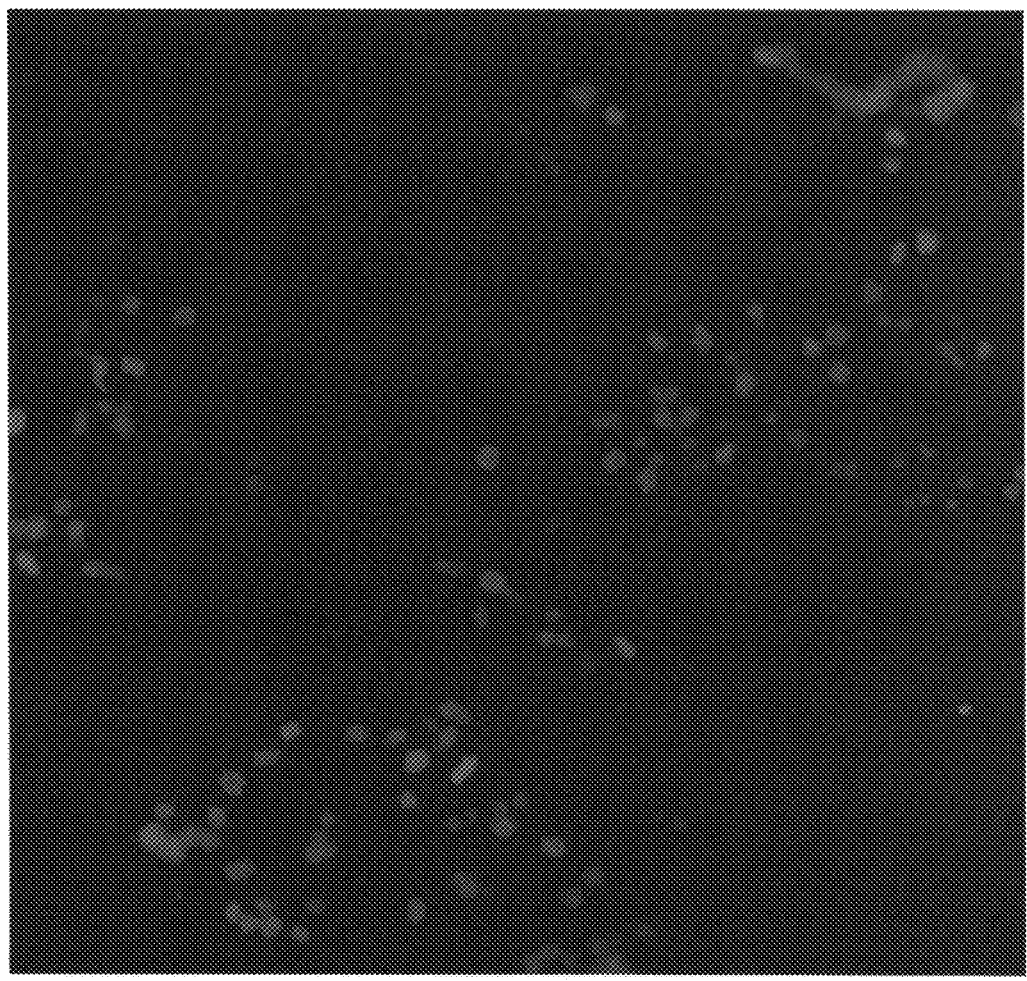
FIG. 2.2C

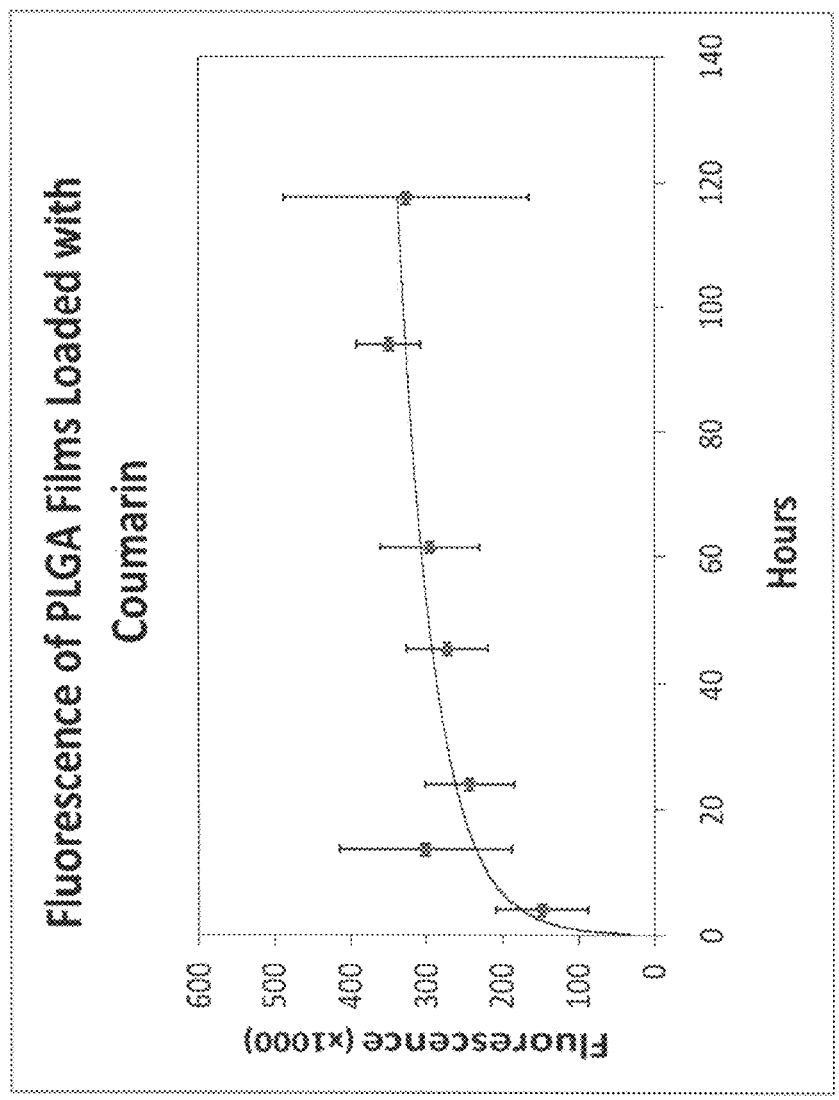
FIG. 2.3

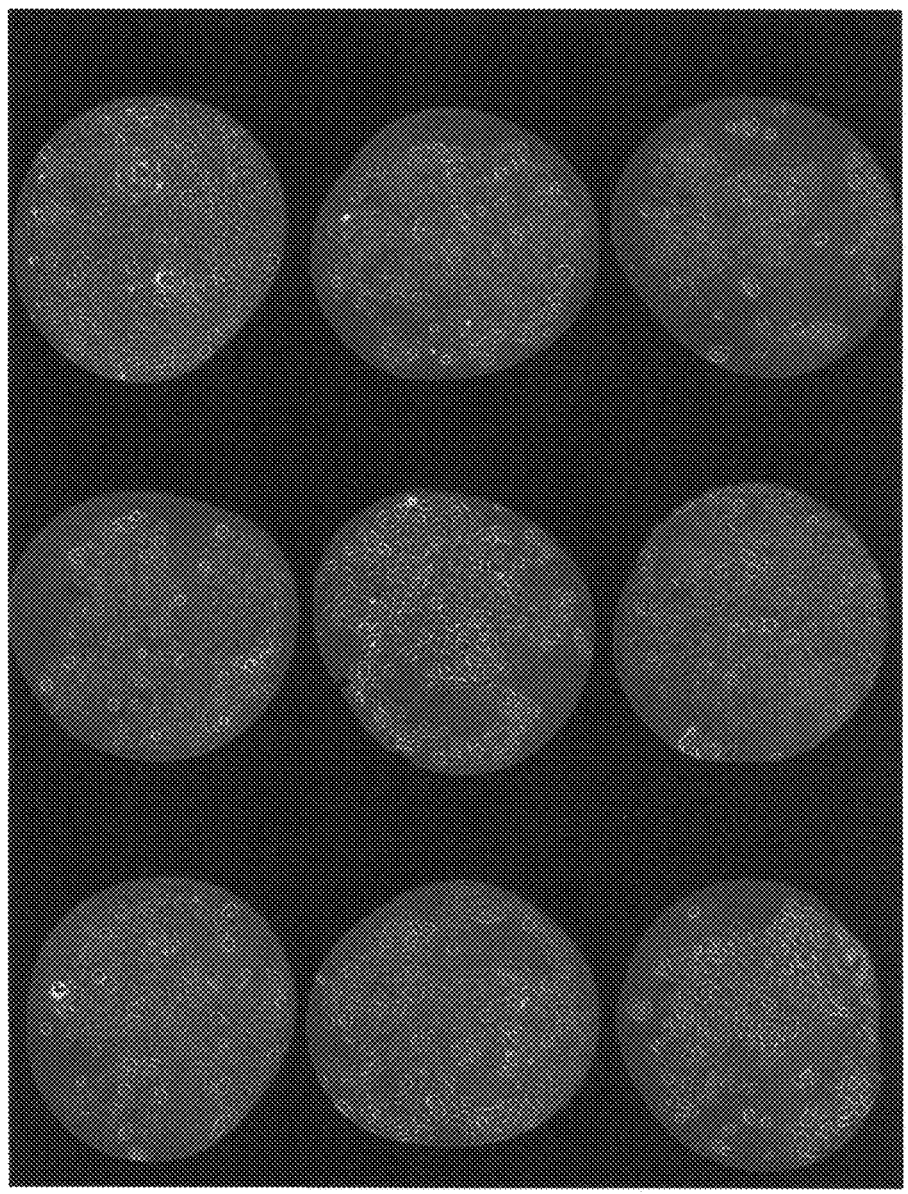
FIG. 3.1

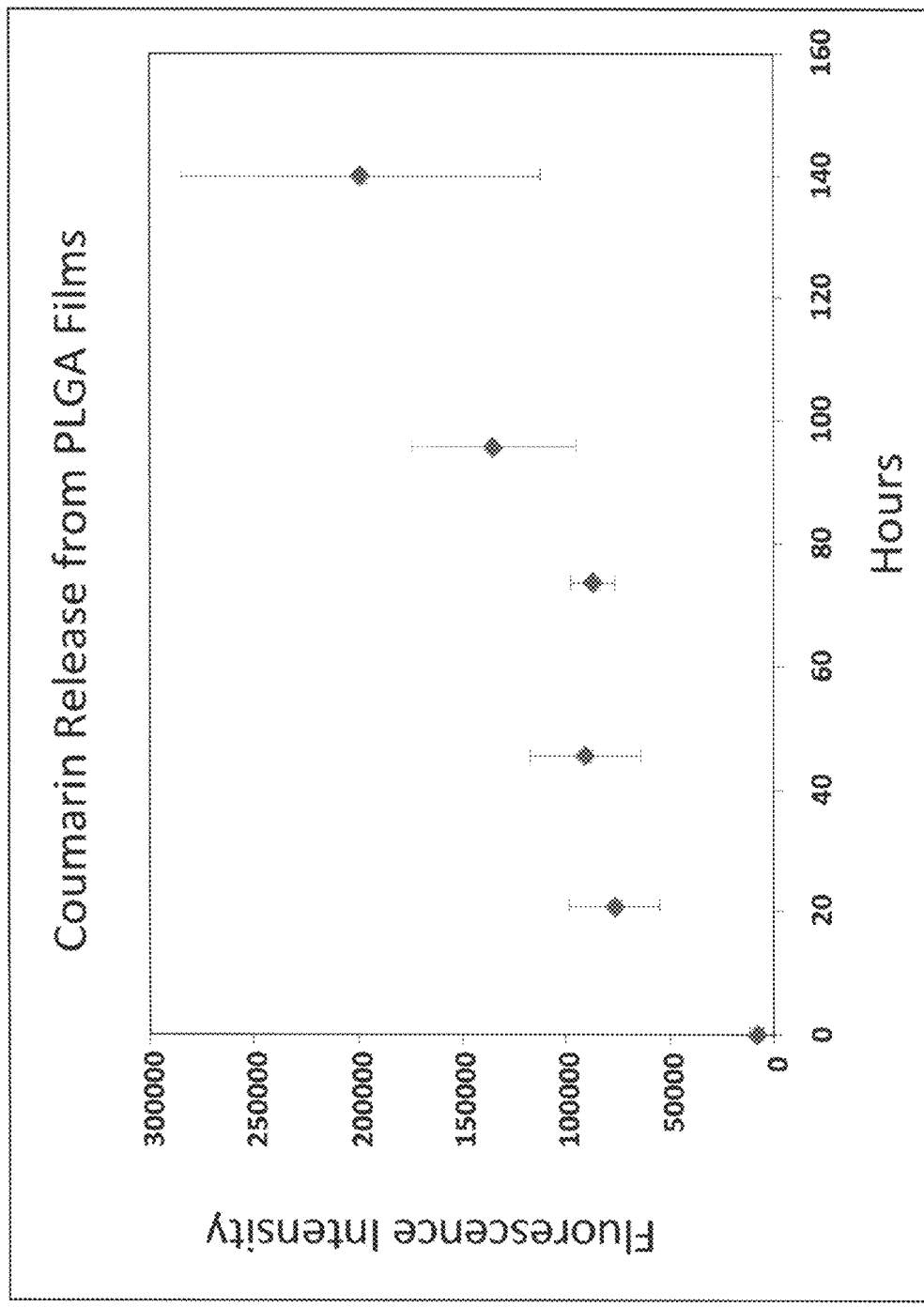
FIG. 3.2

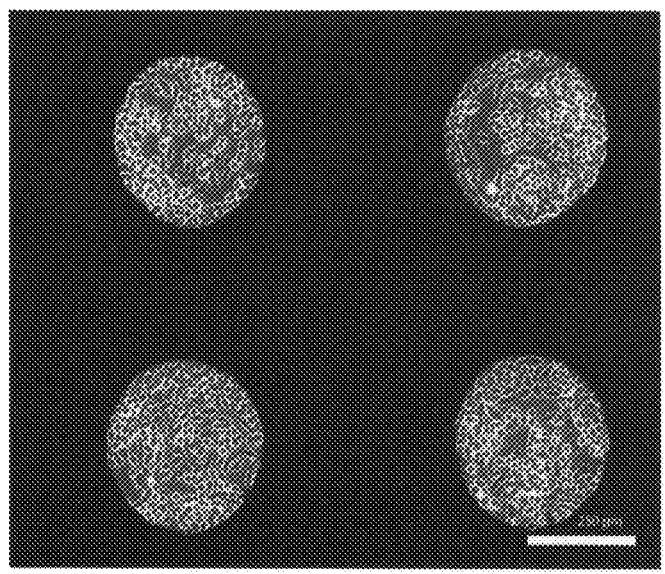
FIG. 4.1
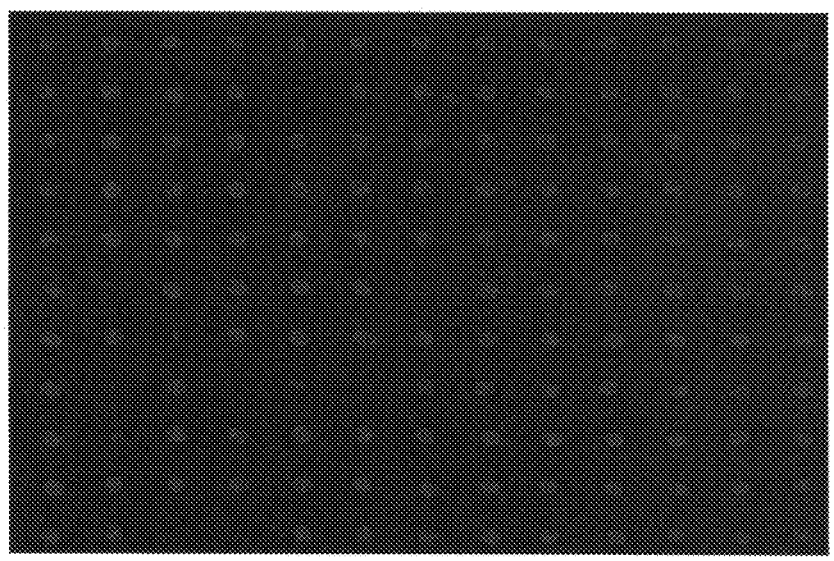
FIG. 4.2

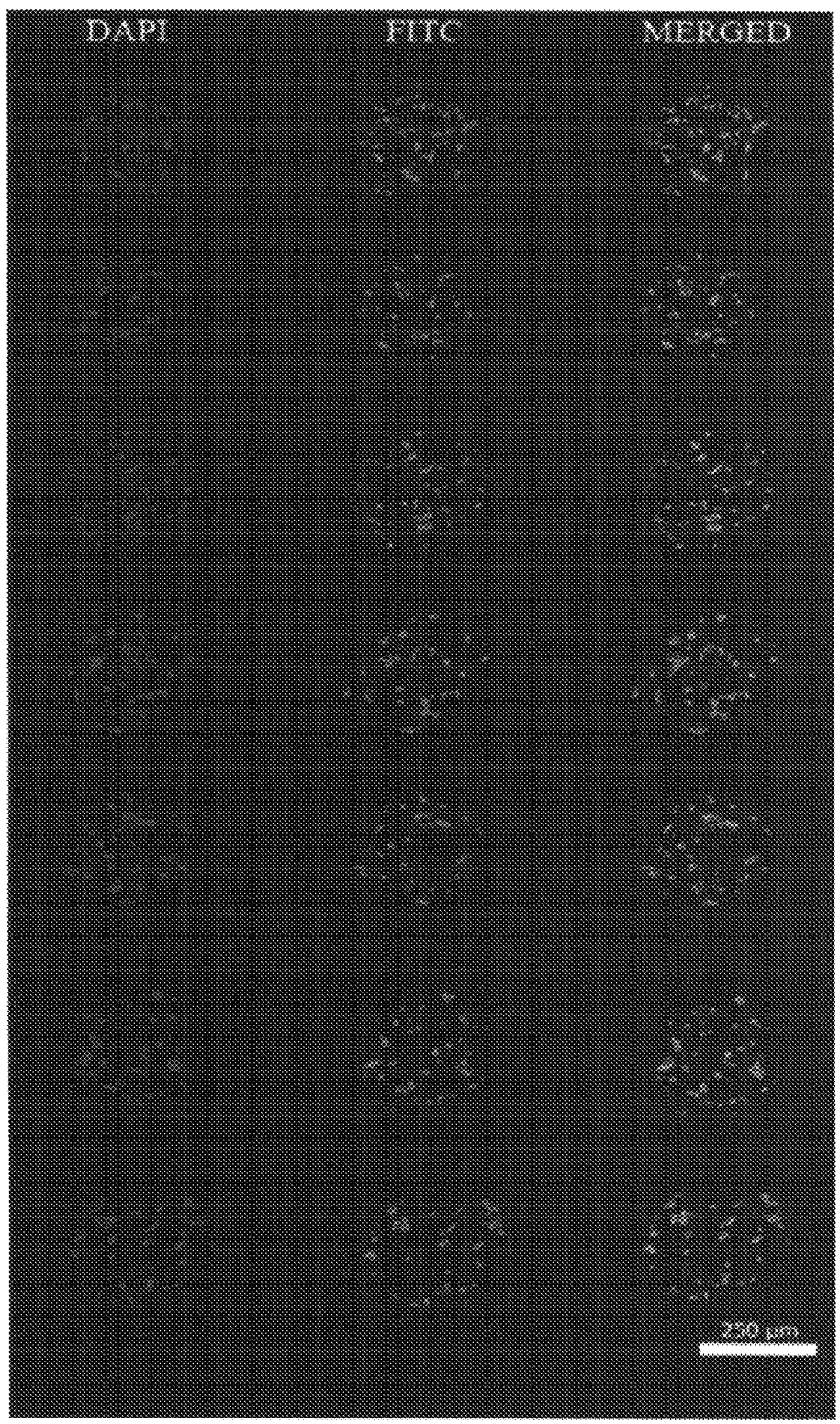
FIG. 4.3

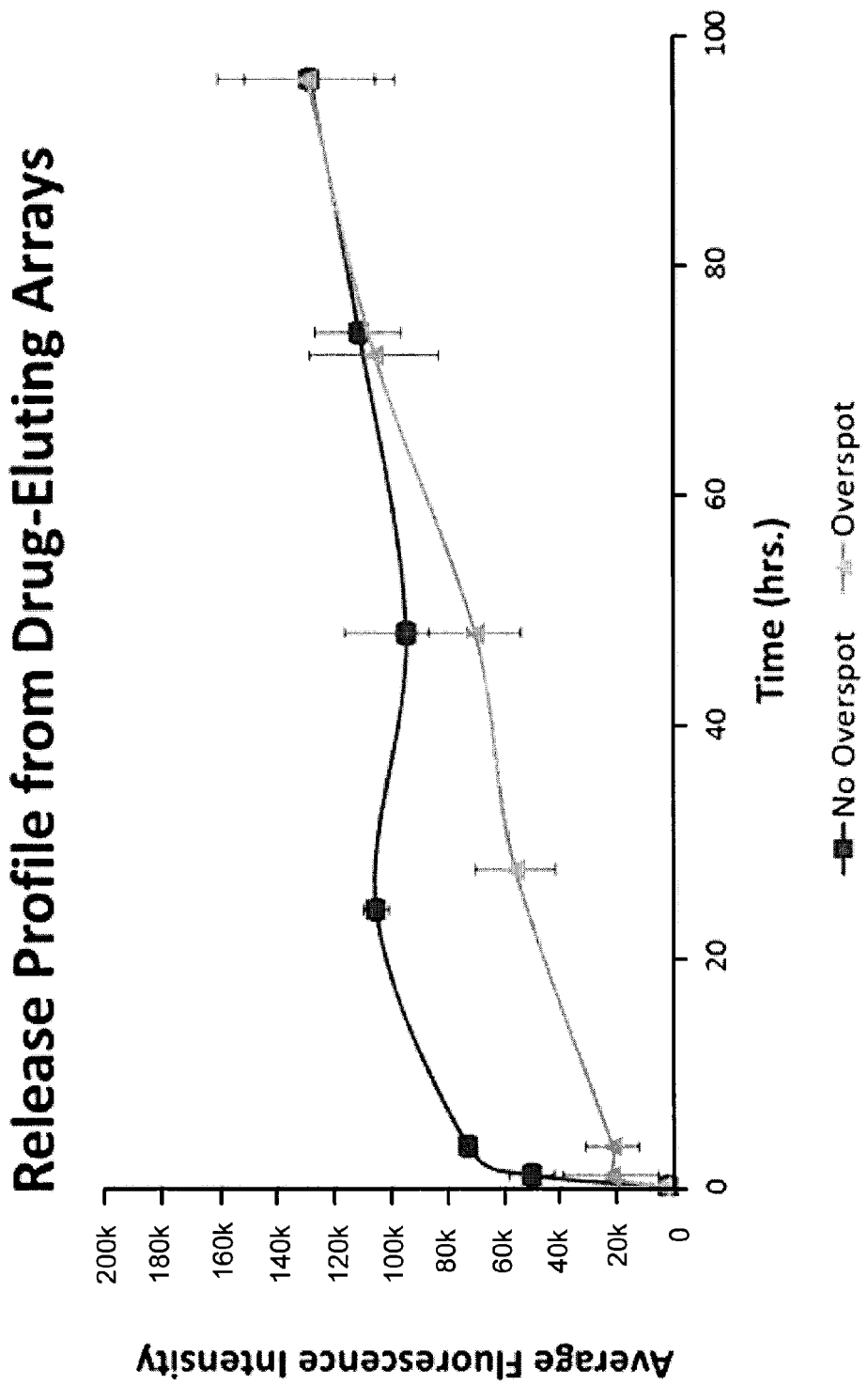
FIG. 4.4

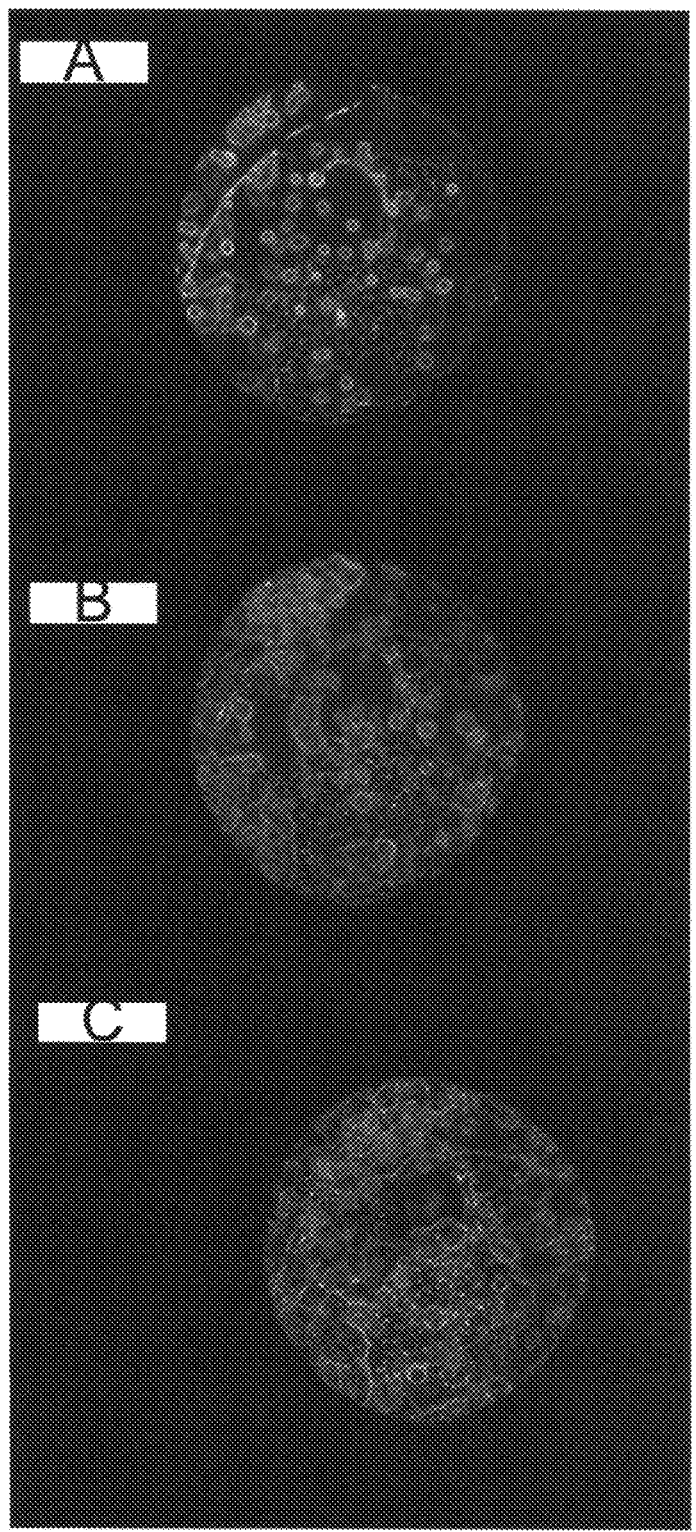
FIG. 5.1A-5.1C

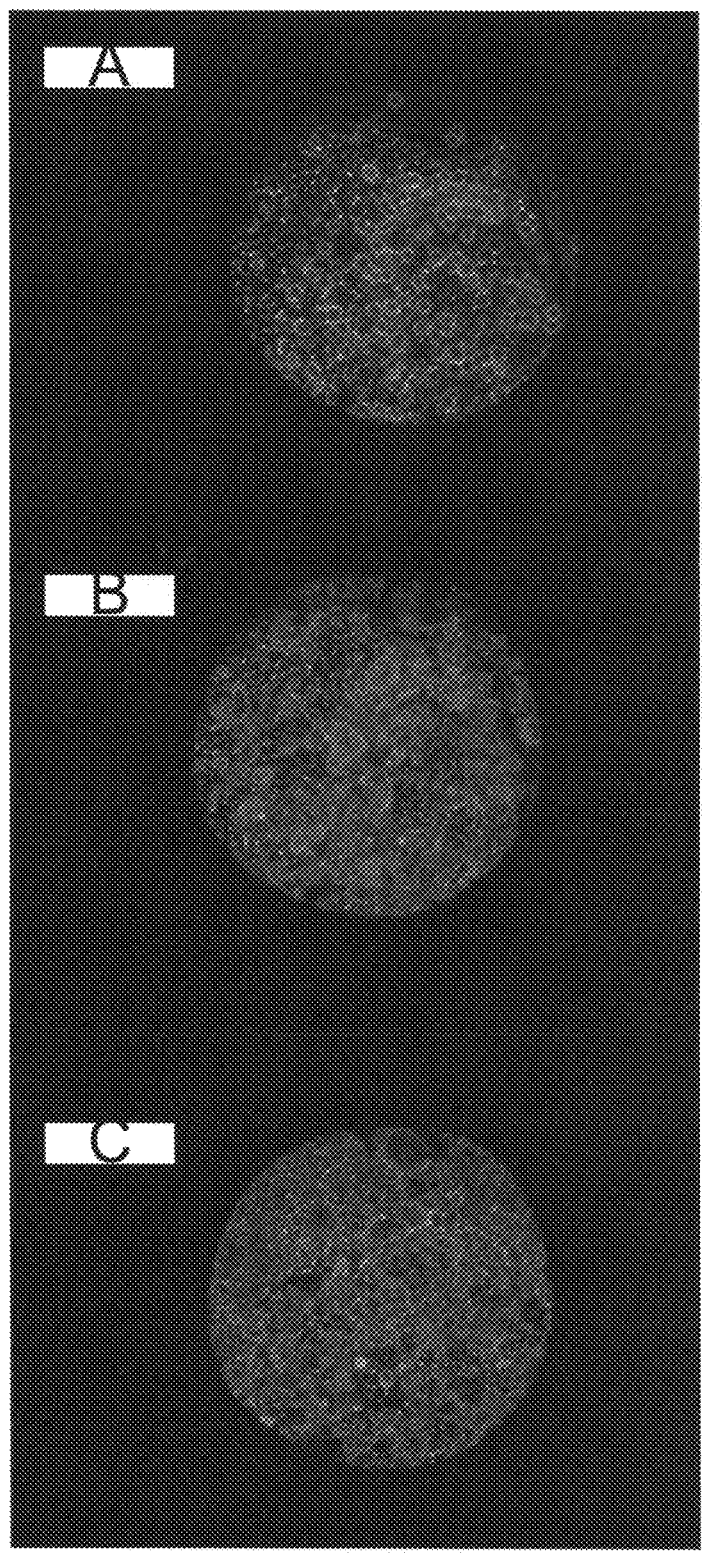
FIG. 5.2A-5.2C

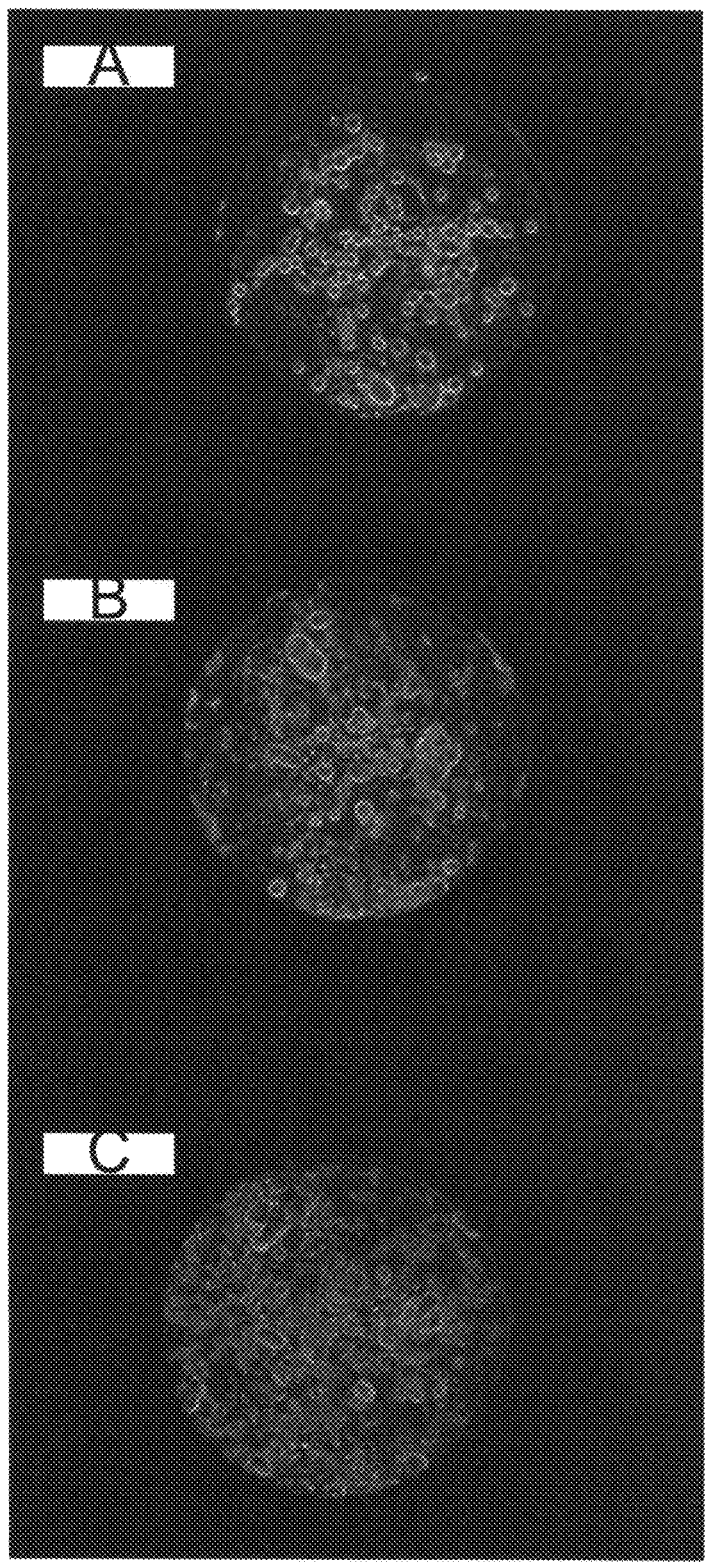
FIG. 5.3A-5.3C

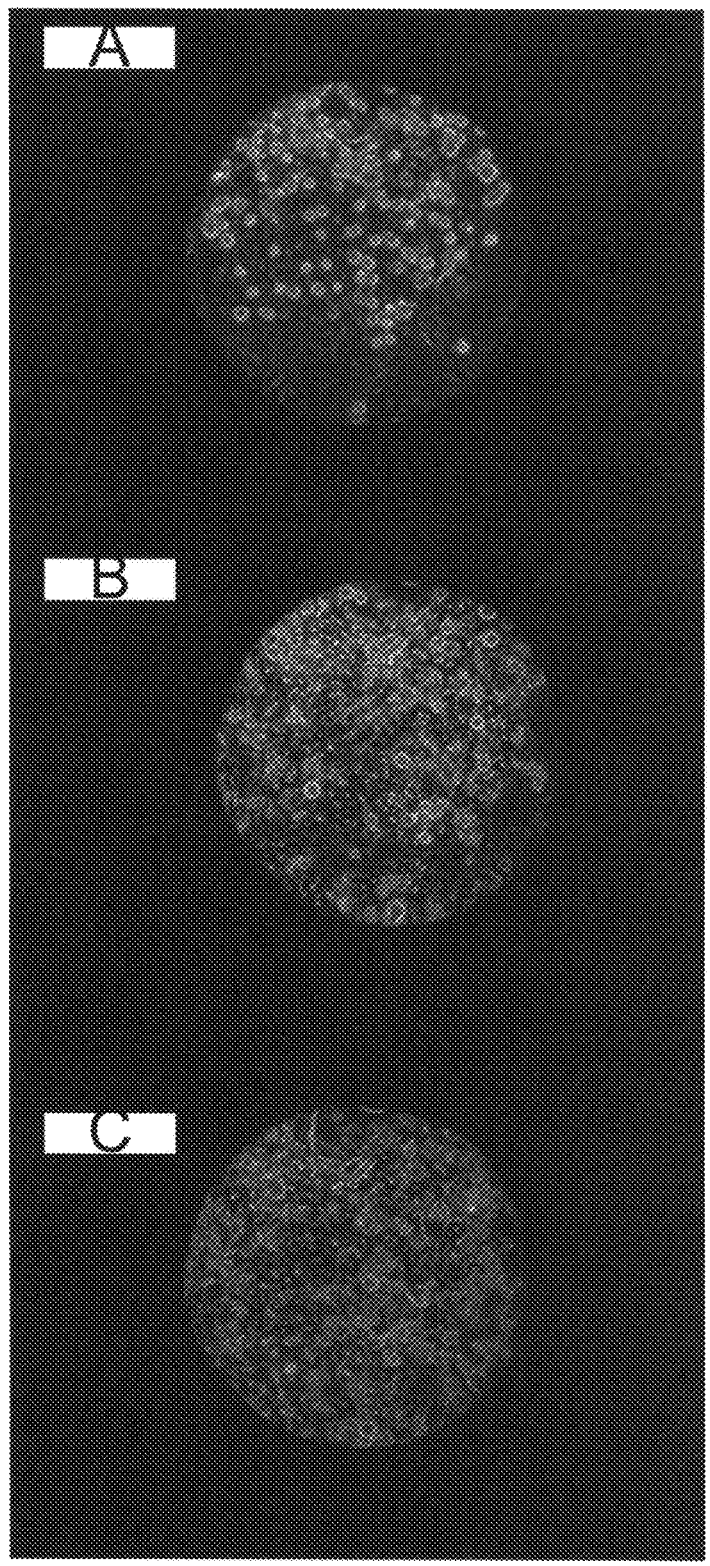
FIG. 5.4A-5.4C

CELL-BASED ARRAYS, METHODS OF MAKING, AND METHODS OF USING

CROSS-REFERENCE TO RELATED APPLICATION

This application claims priority to U.S. provisional application entitled "CELL-BASED ARRAYS, METHODS OF MAKING, AND METHODS OF USING," having Ser. No. 61/409,223, filed on Nov. 2, 2010, which is entirely incorporated herein by reference.

BACKGROUND

Colon cancer is the third most common cause of cancer and cancer death in the United States. Colon cancer stem cells (CCSCs) have only recently been recognized as a potential cause of colon cancer with several markers identified. As such, this cell population has also been targeted for future therapeutics. An obstacle to this approach lies in the fact that CCSCs are rare, and, therefore, it is difficult to screen potential agents.

SUMMARY

Embodiments of the present disclosure provide for arrays, systems, and methods for analyzing cells, methods of making arrays, and the like.

An embodiment of the array, among others, includes: a non-fouling layer disposed in a first area of the array, wherein cells do not substantially adhere to the non-fouling layer; and a plurality of cell binding sites, each being disposed in a cell binding site area of the array distinct from the non-fouling layer, wherein the cell binding sites include a cell adhesion layer and a timed-release polymer layer, wherein each timed-release polymer layer corresponding to a cell binding site includes one or more types of a time released agent, wherein one or more types of target cells adhere to the cell adhesion layer, wherein the timed-release polymer having the characteristic of releasing the agent to the cell or cells adhered to the cell binding site.

An embodiment of the array, among others, includes: a non-fouling layer disposed in a first area of the array, wherein cells do not adhere to the non-fouling layer; and a plurality of cell binding sites, each being disposed in a cell binding site area of the array distinct from the non-fouling layer, wherein the cell binding sites include a cell adhesion layer and a timed-release polymer layer, wherein each timed-release polymer layer corresponding to a cell binding site includes a time released agent, wherein a target cell adheres to the cell adhesion layer, wherein the timed-release polymer having the characteristic of releasing the agent to the cell or cells adhered to the cell binding site, wherein the cell adhesion layer has a thickness of about 0.2 nm to 2 μm, and wherein the timed-release polymer layer has a thickness of about 10 nm to 5 μm.

An embodiment of the array, among others, includes: a first substrate having a first area and a plurality of cell binding site areas, wherein the first area of the array includes: a first bonding layer disposed on the first area of the first substrate; a second bonding layer disposed on the first bonding layer; a non-fouling layer disposed on the second bonding layer, wherein cells do not adhere to the non-fouling layer; and wherein the cell binding site areas are different areas of the first substrate, wherein the cell binding site areas include: an adhesive layer disposed on each of the cell binding site areas of the first substrate; a timed-release polymer layer disposed on the adhesive layer; and a cell adhesion layer disposed on the timed-release polymer layer.

Other structures, arrays, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates a cross-section of an embodiment of the present disclosure.

FIG. 1.2 illustrates a cross-section through the a-a plane of the embodiment shown in FIG. 1.1.

FIG. 1.3A illustrates a schematic of an embodiment of the present disclosure, while FIG. 1.3B illustrates a representative microarray having more than 1000 spots.

FIG. 2.1 illustrates a phase micrograph of an array seeded with murine colon cancer stem cells.

FIGS. 2.2A to 2.2C illustrate micrographs of CCSCs attached to PLGA island imaged using Phase (FIG. 2.2A), DAPI (FIGS. 2.2A and 2.2B), and FITC (FIGS. 2.2A and 2.2C), respectively.

FIG. 2.3 is a graph that illustrates a release profile for PLGA films loaded with coumarin, 355 nm/460 nm.

FIG. 3.1 illustrates human epithelial cells (HCE-T corneal epithelial cells) that are shown seeded on a PLGA film array (over-spotted with adhesion molecules collagen and fibronectin).

FIG. 3.2 illustrates the release over time of coumarin (fluorescent dye) from a chip printed with 169 coumarin-loaded PLGA films.

FIG. 4.1 illustrates a phase contrast/fluorescence overlay micrograph displaying SW480 cells attached to isolated ethylene vinyl acetate (EVA) islands. Cells were seeded onto a small-molecule eluting array and stained with Hoechst 34580.

FIG. 4.2 illustrates a mosaic of SW480 cells seeded onto small-molecule eluting array and stained with Hoechst 34580.

FIG. 4.3 illustrates a micrograph of one column in 7×7 small-molecule-eluting cellular array separated by a fluorescent channel. Arrays were seeded with SW480 cells and stained for BrdU incorporation (green/middle column), indicating proliferating cells, and nuclear counter-stain (blue/left column) 9right-hand column shows both).

FIG. 4.4 illustrates a release profile from arrays printed with 20% (w/w) coumarin-loaded EVA. The upper curve (squares) represents arrays printed with single spots of coumarin-loaded EVA, while the lower curve (triangles) represents a blank EVA film printed over the coumarin-loaded EVA films to delay dye release.

FIGS. 5.1A to 5.1C illustrate HCT116 cells that are nuclear stained with Hoechst over a time of 5 h, 52 h, and 68 h, without any azide present.

FIGS. 5.2A to 5.2C illustrate HCT116 cells that are nuclear stained with Hoechst over a time of 5 h, 52 h, and 68 h, with 37.5 mM azide present.

FIGS. 5.3A to 5.3C illustrate HCT116 cells that are nuclear stained with Hoechst over a time of 5 h, 52 h, and 68 h, with 75 mM azide present.

FIGS. 5.4A to 5.4C illustrate HCT116 cells that are nuclear stained with Hoechst over a time of 5 h, 52 h, and 68 h, with 75 mM azide present.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

Use of the term "affinity" can include biological interactions and/or chemical interactions between or among a material (e.g., a compound or bio-molecule (e.g., polypeptide or polynucleotide)) and a cell. The biological interactions can include, but are not limited to, bonding or hybridization among one or more biological functional groups of the compound or cell. The chemical interaction can include, but is not limited to, bonding among one or more functional groups (e.g., organic and/or inorganic functional groups) located on the compound of cells.

The term "array" encompasses the term "microarray" and refers to an ordered array presented for binding to polynucleotides and the like.

An "array" includes any two-dimensional or substantially two-dimensional (as well as a three-dimensional) arrangement of addressable regions including nucleic acids (e.g., particularly polynucleotides or synthetic mimetics thereof) and the like. Where the arrays are arrays of polynucleotides, the polynucleotides may be adsorbed, physisorbed, chemisorbed, and/or covalently attached to the arrays at any point or points along the nucleic acid chain.

A substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 $cm^2$ or even less than about 10 $cm^2$ (e.g., less than about 5 $cm^2$, including less than about 1 $cm^2$ or less than about 1 $mm^2$ (e.g., about 100 $\mu m^2$, or even smaller)). For example, features may have widths (that is, diameter, for a round spot) in the range from about 10 µm to 1.0 cm. Non-round features may have area ranges equivalent to that of circular features with the foregoing width (diameter) ranges.

An array "package" may be the array plus a substrate on which the array is deposited, although the package may include other features. It will also be appreciated that throughout the present application, that words such as "top," "upper," and "lower" are used in a relative sense only.

An array, such as those described herein, is "addressable" when it has multiple regions of different moieties (e.g., cell binding sites) such that a region at a particular predetermined location (i.e., an "address") on the array can detect a particular outcome for a particular cell type and/or agent, interaction. Array features are typically, but need not be, separated by intervening spaces.

A "scan region" refers to a contiguous (preferably, rectangular) area in which the array features of interest (cell binding sites), as defined above, are found or detected.

An "array layout" refers to one or more characteristics of the features, such as feature positioning on the substrate, one or more feature dimensions, and an indication of a moiety at a given location.

Discussion

In accordance with the purpose(s) of the present disclosure, as embodied and broadly described herein, embodiments of the present disclosure, in one aspect, relate to arrays, systems, and methods for the analyzing cells, methods of making arrays, and the like. In particular, embodiments of the present disclosure include an agent-delivering cell-based array (e.g., microarrays) that can be used to analyze the timed-release delivery of the agent (e.g., drug(s)) to cells such as rare cells (e.g., cancer cells, stem cells, precancerous cells, and the like), any patient-derived cells, or other rare or low population cells.

Embodiments of the present disclosure can permit multiple different biological or pharmaceutical agents and combinations thereof to be tested on rare cell populations. Cell binding sites that include a thin film(s) or layer(s) of timed-released polymer, loaded with an agent(s) of interest, are microarrayed onto a substrate, where the substrate includes a non-fouling layer or background around the cell binding sites that resists or prevents cell adhesion to the non-fouling layer on areas excluding the cell binding sites. Each cell binding site is able to provide a unique agent or combination of agents to be released. In addition, a thousand spots or more may be arrayed onto a single substrate (e.g., standard glass slide).

An embodiment of the array can be implemented with the seeding of a rare cell population of interest onto the array, requiring relatively less cells than alternative systems such as microwell plates and/or microfluidics systems. Non-adherent cells can be removed, thereby providing isolated islands of adherent cells disposed on the cell binding sites in close contact with the timed-release polymer that includes the agent. Outcome parameters of cellular response, including, but not limited to, proliferation, apoptosis, and differentiation using defined agonists/antagonists, are able to be determined through immunostaining or use of a contrast agent, in multiple concentrations of one or more combinations of agents, in the assay. Multiple conditions (e.g., one or more agents in the timed-release polymer, different agents at different cell binding sites, different concentrations of agents at different cell binding sites, and the like) can be evaluated simultaneously using simple common laboratory protocols (with a limited cell number, and without the use of expensive automated microfluidics machines) with application toward personalized medicine (i.e., focused screening of drug interactions with rare cell populations from patients, for example diagnostics for cancer stem cells). Embodiments of this array would lower expenses since fewer reagents/cells would be required, thereby increasing throughput and productivity. These increases would result in more rapid diagnostic capacity.

In an embodiment shown in FIG. 1.1, the array 2 includes a non-fouling layer 4 disposed in a first area of the array 2. The array 2 also includes a plurality of cell binding sites 6. Each of the cell binding sites 6 is disposed in a cell binding site area of the array 2 that is distinct from the non-fouling layer 4. In other words, the non-fouling layer and the cell binding sites areas are separate and distinct areas. Each of the cell binding sites 6 can have an area of about 20 $\mu m^2$ to 5 $mm^2$, where each cell binding site 6 does not have to have the same area. In an embodiment, the area of each cell binding site 6 can be polygonal, circular, semicircular, a combination thereof, or amorphous. Each area of the cell binding site 6 can have the same shape, a combination of shapes, or different shapes. The cell binding sites 6 can be positioned a distance (e.g., about 10 µm to 2 mm or more) from one another so that cross-talk or other interference is substantially reduced or is not exhibited. An array 2 can include a few (e.g., 2, 3, 4, 5, 6, 10, 20, 50, 100, and the like) cell binding sites 6 to a 1000 or more cell binding sites 6 in an area of about 100 $\mu m^2$ to 1,800 $mm^2$ or more for larger array substrates.

Each of the cell binding sites 6 includes a cell adhesion layer 28 and a timed-release polymer layer(s) 26 (additional details provided below). Each timed-release polymer layer 26 corresponding to a cell binding site 6 includes one or more types of a time released agent (e.g., drug, biological, or other agent that can be tested as to its affect on the cell). One or more types of target cells can adhere to the adhesion layer 28. Cells that are not adhered to the cell binding sites 6 can be removed, so only cell binding sites 6 have target cells adhered thereto since the non-fouling layer 4 eliminates or substantially (e.g., about 80%, about 90%, about 95%, about 99%, or about 99.9% or more, in particular about 95% or more) eliminates non-target cells adhering to it.

In an embodiment, the interaction between the cell and the cell binding sites can include electrostatic interactions, van der Waals interactions, hydrogen bonding, hydrophobic interactions, or a combination thereof. In an embodiment, the interaction between the cell and the cell binding sites can also be bound through specific biological binding, covalent binding, and/or entrapment in a gel (e.g., PEG hydrogel, fibrin gel, collagen gel, etc.).

Once the non-adhered cells are removed, the adhered target cells can be exposed over time (e.g., hours to days to weeks) to the agent released from the timed-release polymer layer 26. The effect of the agent on the cells can be studied and analyzed as a function of time. In addition, the effect of the agent on the cells can be studied and analyzed as a function of agent type, combinations of agents, concentrations of agent(s), and the like.

In an embodiment, the target cell of interest may not adhere to a known compound or bio-molecule, but may adhere to another cell type (e.g., fibroblasts, epithelial cells). One way to analyze the target cell is to first adhere a cell that adheres to the target cell to the cell binding site 6. Then the un-adhered cells can be removed, and the target cell of interest can be introduced to the array so that the target cell of interest adheres to the cell on the cell binding site 6. In other words, the cell binding site 6 has a first cell type bonded to the adhesion surface layer 28 and the target cell of interest is adhered to this cell. In another embodiment, the two cells are adhered to one another prior to introduction to the array, and then the cell that adheres to the cell adhesion layer becomes disposed on the cell binding site.

FIG. 1.2 is a cross-section of an array illustrating one cell binding site (a-a plane shown in FIG. 1.1). FIG. 1.3A illustrates a schematic of an embodiment of the present disclosure, while FIG. 1.3B illustrates a representative microarray having more than 1000 spots.

As shown in FIG. 1.2 the array includes a substrate 12 having a first area and a cell binding site area. The first area and the cell binding site areas are different and distinct areas of the first substrate 12. A first bonding layer 14 is disposed on the first area of the first substrate 12. A second bonding layer 16 is disposed on the first bonding layer 14. In an embodiment, one could combine the first bonding layer 14 and the second bonding layer 16 into a single bonding layer. In an embodiment, the non-fouling layer 18 and 22 can be formed of two layers and they are disposed on the second bonding layer 16. In an embodiment, the non-fouling layer 18 and 22 can be attached directly to the substrate 12. An adhesive layer 24 is disposed on each of the cell binding site areas of the first substrate 12. The timed-release polymer layer 26 is disposed on the adhesive layer 24. The cell adhesion layer 28 is disposed on the timed-release polymer layer 26.

The substrate 12 enables imaging live cells and fixed cells, e.g., via brightfield or fluorescence microscopy. In an embodiment, the substrate 12 can be a rigid and optically transparent substrate. In an embodiment, the substrate 12 can be glass (e.g. mica, Pyrex®, and the like); PET, polycarbonate, styrene, and other amorphous polymers; silicon wafer; quartz; and the like. In an embodiment, the substrate 12 can have a thickness of about 0.05 mm to 10 mm. The area of the substrate 12 can vary depending on the desired number of cell binding sites, the distance between the cell binding sites, the size of the cell binding sites, and the like. In an embodiment the area is about 10 mm$^2$ to 1,800 mm$^2$.

The first bonding layer 14 provides a bonding construct for the substrate 12 and the second bonding layer 16. In an embodiment, the first bonding layer 14 can be titanium, nickel, chromium, and the like. The first bonding layer 14 can have a thickness of about 1 nm to 500 nm.

The second bonding layer 16 provides a surface for alkanethiols to form bonds for formation of self-assembled monolayers. In an embodiment, the second bonding layer 16 can be gold, silver, copper, palladium, platinum, nickel, and alloys of any of these. The second bonding layer 16 can have a thickness of about 1 nm to 500 nm.

In an embodiment, the first and second bonding layer could be a single layer that achieves both the functions of the first bonding layer 14 and the second bonding layer 16.

The non-fouling layer (or surface) functions to resist, prevent, or substantially prevent cell attachment in the area that the non-fouling surface is disposed. In an embodiment, the non-fouling layer can be made up of two layers, 18 and 22. In another embodiment, the non-fouling layer can be made of a single layer or multiple layers that achieve the same function as the first layer 18 and the second layer 22.

The first non-fouling layer 18 functions to attach to the second bonding layer 16. In an embodiment, the first non-fouling layer 18 can be made of self-assembled monolayer of methyl-terminated alkanethiol—treatment to promote adsorption of pluronic; hydrophobic polymers (e.g., polyethylene, polyethylene terephthalate, siloxanes); non-polar peptides/amino acids (e.g., alanine, leucine, valine, isoleucine); micro/nano textures; and the like. The first non-fouling layer 18 can have a thickness of about 1 nm to 100 nm.

The second non-fouling layer 22 is attached to the first non-fouling layer 18 and can resist attachment by cells. In an embodiment, the second non-fouling layer 22 can be made of glycol-based polyethylene; a neutral polymer (e.g., poly (2-hydroxyethyl methacrylate, polyacrylamide, poly (N-vinyl-2-pyrolidone, and poly(N-isopropyl acrylamide) (below 31° C.))); an anionic polymer; a phosphoryl choline polymer; gas discharge-deposited coatings (especially from PEG-like monomers); self-assembled n-alkyl molecules with oligo-PEG head groups; self-assembled n-alkyl molecules with other polar head groups; passivating proteins (e.g., albumin and casein); polysaccharides (e.g., hyaluronic acid); liposaccharide; phospholipid mono/bilayers (e.g., phosphorylcholine); glycoproteins (e.g., mucin), and the like. The second non-fouling layer 22 can have a thickness of about 1 nm to 20 μm.

The adhesive layer 24 provides a surface for the timed-release polymer layer 26 and attaches to the substrate 12. In an embodiment, the adhesive layer 24 can be a silane; chemical groups forming covalent bonds to polymer such as: ethylene oxide, acrylamide, other crosslinking schemes; chemical groups promoting non-specific interactions (electrostatic, hydrophobic, van der Waals) such as amine groups (e.g., the amine-terminated silane depicted, polylysine, polyethyleneimmine) or hydrophobic groups (e.g., methyl-terminated silane) or micro/nanotextures; and the like. The adhesive layer 24 can have a thickness of about 1 nm to 500 nm.

The timed-release polymer layer 26 functions to delivers drugs (or agents) and in some instances can promote cell adhesion. In an embodiment, the timed-release polymer layer 26 can be a poly(lactic-co-glycolic acid); polycaprolactone; polyglycolide; polylactic acid; poly(vinylpyridine); chitosan; alginate; and the like. The timed-release polymer layer 26 can have a thickness of about 10 nm to 5 μm. In an embodiment, the timed-release polymer layer 26 can include a plurality of layers each having a thickness of about 10 nm to 5 μm. In an embodiment, the additional layers can function to increase the time that the agent is delivered. In addition to or in the alternative to the timed-release polymer layer 26, the drugs (or agents) can be bound and/or tethered to the one or more layers of the cell binding site to achieve the same function of the timed-release polymer layer. In an embodiment, the cellular uptake can process through a process such as phagocytosis.

The agents can include drugs, compounds, bio-molecules, and the like. The agents can be used to test, study, analyze, and the like, outcomes of the interaction of the agent with the cell. The concentration of the agents can be varied between or among the timed-release polymer layers of the array.

The cell adhesion layer 28 functions to promote adhesion of the cells to the cell binding site by capturing the cells so that the agent can be delivered to the cells. The cell adhesion layer 28 has an affinity for one or more types of cells such as tumor initiating cells, stem cells, inflammatory/immune cells, hematologic cellular components, neural cells, micro-environmental cellular elements, and the like. In an embodiment, the cell adhesion layer 28 can promote adhesion of a specific cell type(s) or can be a material that promotes non-specific binding (e.g., positively-charged treatments such as polylysine, polyethyleneimmine). In an embodiment the cell adhesion layer 28 can include: fibronectin (e.g., endothelia); polylysine (e.g., epithelia); collagen (e.g., epithelia); vitronectin (e.g., fibroblasts); intercellular adhesion molecules (ICAM-1,2,3,4,5); immunoglobulin superfamily Cell Adhesion Molecules (IgSF CAMs) (e.g., dSynCAMs Synaptic Cell Adhesion Molecules (e.g., epithelia), NCAMs Neural Cell Adhesion Molecules (e.g., neural cells), ICAM-1 Intercellular Cell Adhesion Molecule (e.g., leukocytes), VCAM-1 Vascular Cell Adhesion Molecule (e.g., leukocytes), PECAM-1 Platelet-endothelial Cell Adhesion Molecule (e.g., platelets), L1, integrin (e.g., leukocytes); cadherin (e.g., epithelia); and the like. In an embodiment, the cell adhesion layer 28 can have a thickness of about 0.2 nm to 2 μm.

As described above, methods of the present disclosure can include separating cells (e.g., rare cells) from other cells using an array of the present disclosure. Subsequently, the captured cells can be exposed to an agent. In addition, embodiments of the present disclosure include systems using an array of the present disclosure to capture and analyze cells, where the system includes the array and equipment to introduce, remove, etc., reagents and the like.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

As noted above, CCSCs are rare and therefore it is difficult to screen potential agents. In this example we provide an array that can be used to analyze CCSCs (e.g., FIG. 1.3A) using a limited number of cells. This technique utilizes arrays of spotted PLGA films loaded with signaling pathway inhibitors. Signaling pathways govern self-renewal and as such have been identified as a target for therapy. The selected factors include KAAD-Cyclopamine, a sonic hedgehog antagonist; DKK-1, a WNT inhibitor; Compound E, a notch pathway antagonist; and rapamycin, a mTOR inhibitor; Various concentrations were used and factors were printed in randomized arrays in order to factor out potential cross-talk between arrayed spots. Colon stem cells, both cancerous and precancerous, were isolated using ALDH and CD44 expression and identified by cytokine array analyses. Cells were seeded onto colon stem cell inhibitor microarrays, cell attachment was assessed through DAPI staining and proliferation quantified by immunostaining for BrdU incorporation. This example shows that a microarray platform has been developed that allows for a systematic investigation of the role of signaling pathway inhibitors on the response of CCSCs isolated from murine colon crypts, requiring limited cell numbers.

FIG. 2.1 illustrates a phase micrograph of an array seeded with murine colon cancer stem cells. FIGS. 2.2A to 2.2C illustrate micrographs of CCSCs attached to a PLGA island imaged using Phase (FIG. 2.2A), DAPI (FIGS. 2.2A and 2.2B), and FITC (FIGS. 2.2A and 2.2C). FIG. 2.3 is a graph that illustrates a release profile for PLGA films loaded with coumarin, 355 nm/460 nm.

The array can be fabricated using oxygen plasma cleaned coverslips printed with silane in specific array formats. Printed coverslips were coated with 175 Å of titanium followed by 250 Å of gold. Gold coated coverslips were sonicated to expose silane islands. The coverslips were then incubated with methyl-terminated alkanethiol followed by 10% pluronic F-127 to create a nonfouling background. Appropriate drug concentrations were loaded into 10% poly(D,L lactide-co-glycolide) (PLGA) dissolved in polycarbonate. The following drugs were used: Rapamycin—mTOR inhibitor; DKK1—WNT inhibitor; KAAD—Sonic hedgehog inhibitor; Compound E—Notch pathway antagonist; and Wortmannin—P13K. Cell adhesion molecules are then over spotted onto PLGA film islands.

The method of isolating colon cancer stem cell is described below. Colon cancer xenografts were dissociated and colon stem cells, both cancerous and precancerous, were isolated using ALDH, CD44, and ESA expression and identified by cytokine array analyses. Cells are seeded onto array, allowed to attach specifically to islands, and pulsed with BrdU. After 24 h, samples were fixed and stained. Fluorescence and phase contrast micrographs were then taken.

Example 2

Human epithelial cells (HCE-T corneal epithelial cells—representative of an adherent cell type that could be tested) are shown seeded on an PLGA film array (over-spotted with adhesion molecules collagen and fibronectin) (FIG. 3.1). Seeding density was 1 million cells in 3 ml serum-free media, seeding time was approximately 10 minutes, followed by washing to remove loosely-adherent cells from the non-fouling PEG background.

Shown is the release over time of coumarin (fluorescent dye—representative of a small hydrophobic molecule such as many drugs) from a chip printed with 169 coumarin-loaded PLGA films (FIG. 3.2). Characteristics of interest are a burst release within the first 24 hr followed by a more linear release over the next 5 d. These release characteristics are in line with other configurations of PLGA-loaded delivery vehicles (e.g., microparticles, wafers) and are amenable to the cellular array device.

Example 3

FIG. 4.1 illustrates a phase contrast/fluorescence overlay micrograph displaying SW480 cells attached to isolated ethylene vinyl acetate (EVA) islands in a similar manner to methods described for FIG. 3.1 however with a different cell line and different drug-releasing polymer. This is a close-up image of an array similar to that shown in FIG. 4.2. SW480 cells are a human colorectal adenocarcinoma line which are epithelial like in morphology and used as an in vitro model for colorectal cancer. Cells were seeded onto small-molecule eluting array and stained with nuclear stain (blue).

FIG. 4.2 illustrates a whole 11×13 array of SW480 cells seeded onto small-molecule eluting array and stained with nuclear stain (blue). This figure illustrates high specificity of cell adhesion onto small-molecule releasing islands with little off-spot adhesion across the entire array.

FIG. 4.3 illustrates one column in an array similar to that in FIG. 4.2. This array was seeded with SW480 cells and incubated for 4 days. At 80 hours post seeding, the array was pulsed with BrdU for 16 hours and later stained for BrdU incorporation (green/middle column), indicating proliferating cells, and nuclear counter-stain (blue/left-hand column).

This figure displays the spots separated by fluorescent channel and a final merged image (right-hand column).

FIG. 4.4 illustrates a release profile from arrays printed with 20% (w/w) coumarin-loaded EVA. The methods were similar to those from FIG. 2.3 with exception of the over-spotted samples illustrated by the green curve (triangles). The red curve (squares) represents arrays printed with single spots of coumarin-loaded EVA, while the green curve represents an extra layer of polymer over-spotted to delay release of the loaded factor.

Example 3

The following figures (FIGS. 5.1 to 5.4) are micrographs taken from drug-eluting cellular microarrays, manufactured as described herein. The images are taken from individual cellular islands from the same array under various drug-loading conditions over a period of three days. HCT116 cells are nuclear stained with Hoechst for easy visibility. All polymer formulations have 5% ELVAX in cyclohexanol (w/w) loaded with 8.5% water phase (loaded with drug) and 8.5% polyvinyl alcohol (to form a stable emulsion). The water phase for this experiment was loaded with azide at various concentrations in addition to a control with no drug loaded. Azide is a useful probe reagent, mutagen, and preservative. Azide inhibits cytochrome oxidase by binding irreversibly to the heme cofactor in a process similar to the action of carbon monoxide. As such, it is expected to induce necrosis in cells at physiologically relevant doses. Our array demonstrates a dose-dependent response to azide as shown in FIGS. 5.1 to 5.4. In the absence of azide (Blank ELVAX), the attached cells appear viable after 68 hour incubation. However, in the presence of azide, cell death is evidenced by the decrease in cell density, which is intensified at the higher concentrations.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

Therefore the following is claimed:

1. An array, comprising:
    a substrate having a first area of the array and a plurality of cell binding site areas distinct from the first area;
    a first bonding layer disposed on the substrate in the first area of the array, wherein the first bonding layer is selected from the group consisting of: titanium, nickel, chromium, and a combination thereof;
    a second bonding layer disposed on the first bonding layer, wherein the second bonding layer is selected from the group consisting of: gold, silver, copper, palladium, platinum, nickel, alloys of each of these, and a combination thereof;
    a non-fouling layer disposed on the second bonding layer in the first area of the array, wherein cells do not substantially adhere to the non-fouling layer; and
    a plurality of cell binding sites corresponding to the cell binding areas, each cell binding site comprising:
        an adhesive layer disposed on the substrate in each cell binding site area of the array distinct from the non-fouling layer,
        a timed-release polymer layer disposed on the adhesive layer in each cell binding site, each timed-release polymer layer comprising one or more thin films, each thin film including one or more types of a time released agent, wherein the timed-release polymer layer of at least one cell binding site comprises at least one type of agent different from at least one type of agent in the timed-release polymer layer of at least one other cell binding site, and
        a cell adhesion layer disposed on the timed-release polymer layer in each cell binding site, wherein one or more types of target cells adhere to the cell adhesion layer, the timed-release polymer layer having the characteristic of releasing the agent to the cell or cells adhered to the cell binding site.

2. The array of claim 1, wherein one of type target cell, a first target cell, has an affinity for another type of target cell, a second target cell, wherein both the first target cell and the second target cell are disposed on the cell binding site, the timed-release polymer having the characteristic of releasing the agent to the first target cell and the second target cell adhered to the cell binding site.

3. The array of claim 1, wherein the cell binding sites have an area of about 20 $\mu m^2$ to 5 $mm^2$ and wherein a pair of cell binding sites is positioned about 10 $\mu m$ to 2 mm from one another.

4. The array of claim 1, wherein one type of target cell adheres to the cell adhesion layer.

5. The array of claim 1, wherein the non-fouling layer comprises two layers, wherein a first layer of the non-fouling layer is made of a methyl-terminated alkanethiol, and wherein a second layer of the non-fouling layer is made of a material selected from the group consisting of: a glycol-based polyethylene, a neutral polymer, an anionic polymer a phosphoryl choline polymer, a gas discharge-deposited coating, a self-assembled n-alkyl molecule with oligo-PEG head groups, a self-assembled n-alkyl molecule with other polar head groups, a passivating protein, a polysaccharide, a liposaccharide, a phospholipid mono/bilayer, a glycoprotein, and a combination thereof.

6. The array of claim 1, wherein the first bonding layer has a thickness of about 1 nm to 500 nm.

7. The array of claim 1, wherein the second bonding layer has a thickness of about 1 nm to 500 nm.

8. The array of claim 1, wherein the adhesive layer is selected from the group consisting of: a silane, a compound including an ethylene oxide group, a compound including a acrylamide group, a compound including an amine group, a compound including a hydrophobic group, and a combination thereof.

9. The array of claim 8, wherein the adhesive layer has a thickness of about 1 nm to 500 nm.

10. The array of claim 1, wherein the timed-release polymer layer is selected from the group consisting of: a poly(lactic-co-glycolic acid), polycaprolactone, polyglycolide, polylactic acid, poly(vinylpyridine), chitosan, alginate, and a combination thereof.

11. The array of claim 10, wherein the timed-release polymer layer has a thickness of about 10 nm to 5 μm.

12. The array of claim 1, wherein the timed-release polymer layer includes a plurality of layers each having a thickness of about 10 nm to 5 μm.

13. The array of claim 1, wherein the cell adhesion layer is selected from the group consisting of: fibronectin, polylysine, collagen, vitronectin, intercellular adhesion molecules, immunoglobulin superfamily Cell Adhesion Molecules (IgSF CAMs), Neural Cell Adhesion Molecules (NCAMs), Intercellular Cell Adhesion Molecules (ICAM-1), Vascular Cell Adhesion Molecules (VCAM-1), Platelet-endothelial Cell Adhesion Molecules (PECAM-1), L1 Cell Adhesion Molecules (L1), integrin, cadherin, and a combination thereof.

14. The array of claim 13, wherein the cell adhesion layer has a thickness of about 0.2 nm to 2 μm.

15. The array of claim 1, wherein the time release agent is not DNA.

16. An array, comprising:
a substrate having a first area and a plurality of cell binding site areas distinct from the first area, wherein the first area of the array includes:
  a first bonding layer disposed on the first area of the first substrate;
  a second bonding layer disposed on the first bonding layer;
  a non-fouling layer disposed on the second bonding layer, wherein cells do not adhere to the non-fouling layer; and
wherein the cell binding site areas include:
  an adhesive layer disposed on each of the cell binding site areas of the first substrate;
  a timed-release polymer layer disposed on the adhesive layer, wherein the timed-release polymer layer comprises one or more thin films including one or more agents, wherein the timed-release polymer layer of at least one cell binding site comprises at least one type of agent different from at least one type of agent in the timed-release polymer layer of at least one other cell binding site; and
  a cell adhesion layer disposed on the timed-release polymer layer.

17. The array of claim 16, wherein the time release agent is not DNA.

* * * * *